(12) United States Patent
Fang

(10) Patent No.: US 10,071,258 B2
(45) Date of Patent: Sep. 11, 2018

(54) DNA OXIDATIVE DAMAGE REPAIRING DEVICE AND APPLICATION METHOD THEREOF

(71) Applicant: Moxi Fang, Beijing (CN)

(72) Inventor: Moxi Fang, Beijing (CN)

(*) Notice: Subject to any disclaimer, the term of this patent is extended or adjusted under 35 U.S.C. 154(b) by 151 days.

(21) Appl. No.: 15/307,615

(22) PCT Filed: Apr. 10, 2015

(86) PCT No.: PCT/CN2015/076301
§ 371 (c)(1),
(2) Date: Oct. 28, 2016

(87) PCT Pub. No.: WO2015/165327
PCT Pub. Date: Nov. 5, 2015

(65) Prior Publication Data
US 2017/0189705 A1   Jul. 6, 2017

(30) Foreign Application Priority Data

Apr. 29, 2014 (CN) .......................... 2014 1 0175924

(51) Int. Cl.
*A61N 1/44*   (2006.01)
*A61N 1/04*   (2006.01)
(52) U.S. Cl.
CPC ............. *A61N 1/44* (2013.01); *A61N 1/0468* (2013.01); *A61N 1/0476* (2013.01)
(58) Field of Classification Search
None
See application file for complete search history.

(56) References Cited

FOREIGN PATENT DOCUMENTS

| CN | 1230444 A | 10/1999 |
|---|---|---|
| CN | 1382503 A | 12/2002 |
| CN | 1439435 A | 9/2003 |
| CN | 103920237 A | 7/2014 |

*Primary Examiner* — Brian T Gedeon
(74) *Attorney, Agent, or Firm* — Hodgson Russ LLP

(57) ABSTRACT

Disclosed are a DNA oxidative damage repairing device and an application method thereof. The device is composed of an electrons emitting assembly, an electrons emitting electrode, a control system, a power source, a support and the like. The device emits electrons to a space in a certain range, negatively charged nano particles with certain density are formed in the space, the space is sterilized, and various hazardous substances in suspension space are eliminated. The negatively charged nano particles entering a body through a respiratory system release electrons carried by the particles, electrons lost due to oxidative damage are replenished to all parts of the body, and dormant state genes can also be repaired and activated. The two-way regulations function can play a role in broad spectrum medical treatment, so that diseases that cannot be cured through drugs easily are present are cured. The device has an obvious curative effect on diseases caused by immune function deficiencies, diseases of a respiratory system, various wounds, diseases caused by drug addiction treatment and the like. The method is combined with correct and effective using of suppressing drugs and accurate using of traditional Chinese medicine, and accordingly a novel hopeful therapeutic scheme of treating AIDS, cancers and various genetic diseases before histone codes are deciphered can be provided.

1 Claim, 2 Drawing Sheets

DNA OXIDATIVE DAMAGE REPAIRING DEVICE AND APPLICATION METHOD THEREOF

FIELD OF THE INVENTION

The present invention relates to a brand new physical therapy device and a method thereof, and more particularly, to a physical therapy device capable of curing various diseases that cannot be cured by clinical medicines and other methods nowadays.

BACKGROUND OF THE INVENTION

In contemporary clinical medicine, chemical drugs are served as a main concept and method for disease treatment, but the chemical drugs have different toxic and side effects, causing varying degrees of damage to human health. The key is that a variety of complicated and refractory diseases caused by cancers, genetic diseases, chronic respiratory diseases, cell death and the like cannot be cured by the contemporary clinical medicine, resulting in many premature deaths.

Therefore, a new physical therapy needs to be quickly launched, without any toxic and side effects. The clinical practice has proved that a physical therapy can cure various complicated and refractory diseases that cannot be cured by today's clinical medicine and it has a broad spectrum of medical treatment effect.

According to reports of the World Health Organization, non-infectious diseases are a "first killer" in today's world. In 2008, for example, 63 percent of the death of the world's population, about 36 million people, died of the non-infectious diseases, while 80% of which occurs in low- and middle-income countries. If no action is taken, it is expected that the epidemic of non-infectious diseases by 2030 will make 52 million people died.

With analysis, it's believe that the cause of death and non-infectious diseases, particularly the formation of disease, has a direct correlation with four factors, in which: environmental factors; food chain in a region and a country and eating habits; good habits and exercise; preventive measures and treatment measures adopted. Most experts and the World Health Organization (WHO) have similar or even identical views about the four related factors. The problem is that chemical drugs are dominant in disease prevention and therapeutic method of disease, but it is difficult to achieve the purpose of prevention and cure by using the chemical drugs for cancers, genetic diseases, and diseases caused by immune function deficiencies. We need to explore new ideas, and propose new concepts and methods to solve the problems that cannot be solved by today's clinical medicine.

In 1950s, a DNA structure of double helix is discovered. After nearly 60 years of research, scientists have found that free radicals and other by-products produced by metabolism (including aerobic respiration) may cause different types of oxidative damage to a DNA base pair and take away electrons in a double helix base pair structure. If failing to repair in time, it may cause serious problems, such as if oxidized guanine react with water molecules, miss match of the base will be formed, that is to say gene mutation occurs. Scientists have found that variation caused by base oxidation is a major reason for cancers, genetic diseases and cell death.

It has to be clearly understood that oxidative damage caused by free radicals and other by-products produced by metabolism (including aerobic respiration) is ever-present. In addition, with respect to the damage caused by enabling ionizing radiation, ultraviolet radiation, chemicals in smoke (including tobacco), from the external environment, and other pollutants in the air environment to enter into the body; and the damage caused by enabling various pollutants from the food chain (including water) to enter into the body, humans can take various measures to reduce the damage, but cannot avoid damage after these external factors enter into the body. If these external factors enter into the body, the oxidative damage to the body will be exacerbated. The human body has a strong ability to repair itself, biologists now has confirmed or suspected over 130 human genes associated with DNA repair, and this figure is still increasing. However, any repair of oxidative damage is related with electrons, and the electrons play an important role in DNA repair. Therefore, it is necessary to replenish the electrons for the body.

Today thousands of people died of non-infectious diseases worldwide each year are directly associated with the DNA oxidative damage. It's proposed in a patent titled "apparatus and method for producing negatively charged nano particles" that how to produce the negatively charged nano particles. However, it does not definitely teach that the electrons can clean up and sterilize an ambient space within a certain range, and work in a body after the negatively charged nano particles entering into the body, in addition to produce the negatively charged nano particles in the air. To this end, it becomes a new method for repairing the DNA oxidative damage.

SUMMARY OF THE INVENTION

The present invention provides a device and an application method thereof, with a brand new physical conception and method of providing electrons for a body. The electrons entering the body reach the whole body through blood circulation to participate in an electric metabolic process of tissue-cell-molecular level and function in two aspects including: replenishing the electrons lost due to DNA oxidative damage; and supplying electrons to the enzymes which offer the electrons for repairing oxidative damage in a repairing system at the same time. In this way, gene mutation of DNA caused by oxidative damage can be avoided, and at the same time the repairing gene in a dormant state due to a loss of electrons can be repaired and activated.

According to exemplary embodiments of the present invention, a DNA oxidative damage repairing device comprises an electrons emitting electrode, a support, a control system, a power source, a housing and a box body, a support wheel-leg or a support leg or a support plate, and an electrons emitting assembly, wherein the electrons emitting assembly is connected with the support, the support is connected with the housing and the box body, both the control system and the power source are connected with the housing or the box body, the housing or the box body is connected with the support wheel-leg or the support leg or the support plate; the electrons emitting electrode is contained in the electrons emitting assembly; the device only emits electrons to a space that is greater than 20 m$^3$ and less than or equal to 100 m$^3$, and does not emits any other substances.

The electrons emitting assembly (including electrons emitting electrode, emitting window and other parts) may emit the electrons to the space by adopting different materials, sizes, structure and shape constitution and applying a mechanism of tunnel effect, according to various applications and needs. The support of the electrons emitting device may be a movable or a fixed support; the support, the housing, the box body, the power source and the control system may be either uniformly considered to design as a whole in structure, size and shape, or separated as respectively independent parts; and a manual or remote control mode or both of the two may be adopted between different power lines and the control system, according to the needs.

Electrons emitted by the electrons emitting device are combined with oxygen molecules, carbon dioxides molecules, water vapor molecule in air or with a molecular group composed of these molecules or with a nano molecular groups composed of these molecules and other molecules in air, to form negatively charged nano particles, the density of the negatively charged nano particle formed within a space range of greater than 20 $m^3$ and less than or equal to 100 $m^3$ is greater than $5 \times 10^3$ $cm^3$ and less than or equal to $1.5 \times 10^9$ $cm^3$. The negatively charged nano particles formed with in the space range are combined with various pollutants suspended in the air (including various chemical pollutants, toxic and harmful substances, and radioactive substances) into particles of greater than 5 um through polymerization. These particles are sedimentated under gravity and electric field force so as not to suspend in the space and do harm to a human body; the negatively charged nano particles also kill bacterias and viruses within this range to sterilize the space within this range. At the same time, a user inhales and receives the negatively charged nano particles through a respiratory system (including respiratory tract, skin, ears, nose, eyes, and navel) in a pollution-free sterilization space. The negatively charged nano particles entering the body release the electrons carried by the particles, although oxygen molecules, carbon dioxide molecules, water vapor molecules or other molecules are still exchanged through metabolism. The electrons reach the body through the blood circulation, providing the electrons for all parts of the body, and participating in the electric metabolic process throughout the tissue-cell-molecular level; regulating the potential balance of tissue cells; and improving the body's natural physiological state and biochemical environment. These electrons entering the body are supplied for the repair of DNA oxidative damage, and at the same time, supplied to the repairing genes that lose electrons, so as to repair and activate the genes in the dormant state, such that the genes in each repairing system are in a normal working condition. The vitality of the immune cells is repaired and activated, the bacterias and viruses entering the body are killed, various "mutant" cells are eliminated, and various organs of the body are protected and working in normal.

An external environment condition can be effectively improved to protect health. An internal environment condition of the body is regulated and improved, and the genes in the dormant state due to the loss of electrons are repaired and activated at the same time, a two-way regulation function is provided, so that a broad spectrum of medical function and effect is realized. As metabolism occurs at all times, various other oxidative damage also occurs at all times, the electrons are necessarily to be replenished for a healthy person, a sub-healthy person and a patient in time. The electrons are replenished to prevent a disease for a healthy person; the electrons are replenished for a sub-healthy person to regulate and help recuperate his health; the electrons are replenished for a patient to help curing a disease and recuperate his health. Of course, an electrons introducing mode, amount of electrons and practice to these three types of people should be completely different. The device is a device integrating prevention, health protection, rehabilitation and treatment as a whole. Therefore, the device has various names due to the action, function and effect of curing various diseases, and due to the adopted structure, shape, theoretical deduction or some self-creation, however, it is still essentially an electrons emitting device.

To maintain life activities of a human body, energy, various substances, water and air are needed to replenish. As mentioned, the occurrence of a disease is associated with four factors. Humans can take a variety of measures to minimize various damages as far as possible, but cannot completely eliminate the damages, so that these damage factors that cannot be completely eliminated and the damage caused by free radicals produced by metabolism of human body and other by-products are main reasons for damaging health and resulting in disease. Currently the primary means for disease treatment is to use a variety of drugs. The drugs are taken as a primary therapeutic method and served as the unique therapeutic method for some diseases. A large number of research to clinical medicines have demonstrated that many drugs are double-edged swords, their therapeutic effects and damages to the body organs coexist, so that it is absolutely necessary to change the way of thinking and eliminate the single solution of adopting the drugs to cure the diseases. Thousands of years of history in the survival of mankind and the results of a large number of research by biologists for nearly 60 years have proved that a lot of people still can survive in good health for decades or even more than 100 years from oxidative damage caused by the free radicals produced by metabolism of the body and the other by-products as well as various damages caused by the complicated natural environment, that is because the body has a strong ability to repair itself. At present, there are more than 130 repairing genes that have been found to constitute a specific repair system, and each of them is respectively responsible for repairing a special damage. Repairing and activating these genes in a dormant state is a better and more important approach than taking drugs for the treatment of some diseases. After years of observations to clinical medicines and effects of disease cure, the practice has initially proved that the electrons emitting device can play a role in repairing.

Bacteria and viruses can be killed efficiently, by combing the following three measures: using the two-way regulation of the electrons emitting device, correctly and effectively utilizing an inhibiting function of current drugs, applying accurately the recuperation, regulation and energy replenishing of traditional Chinese medicine acupuncture point, traditional Chinese medicine and food therapy thereof. A complicated mode of a chemical radical in a histone is regulated, improved and repaired, so as to accurately control the genes and coordinate information and activities of a whole genome, and repair and activate various organ-specific repairing systems in the body. It will be a novel hopeful therapeutic scheme for treating AIDS or HIV carriers, cancers or cancer post-operation and various genetic diseases before histone codes are deciphered.

The present invention is advantageous over the prior art in that: according to clinical observation, for different diseases, it is crucial to adopt different treatment times, treatment methods, treatment locations as well as different densities of negatively charged nano particles, during a treatment. The density of the negative charged nano particles is directly related to the electrons emitted by the electrons emitting device. In order to make the electrons emitting device emit the electrons with different densities, the electrons emitting assembly and the electrons emitting electrode in the electrons emitting device adopt different materials, structures, shapes and sizes. The electrons emitting electrode is a part of the electrons emitting device as well as a unique electrode having a potential in the whole electrons emitting device with respect to a ground potential outside the device, and it only emits the electrons to the space outside the device and does not emit any other substances. These electrodes may consist of a single or a plurality of electrodes having the same potential. According to the density of electrons emitted as required and different materials, structures, shapes and sizes of the electrons emitting electrode, the electrons emitting electrode is provided with a potential of −2 kv to −45 kv relative to the ground potential outside the electrons emitting device. An external environment condition can be effectively improved to protect health. An internal environment condition of the body is regulated and improved, and the genes in the dormant state due to the loss of electrons are repaired and activated at the same time, a two-way regulation function is provided, so that a broad spectrum of medical function and effect is realized. As metabolism occurs at all times, various other oxidative damage also occurs at all times, the electrons are necessarily to be replenished for a healthy person, a sub-healthy person and a patient in time. The electrons are replenished to prevent a disease for a healthy person; the electrons are replenished for a sub-healthy person to regulate and help recuperate his health; the electrons are replenished for a patient to help curing a disease and recuperate his health. Of course, an electrons introducing mode, amount of electrons and practice to these three types of people should be completely different. The device is a device integrating prevention, health protection, rehabilitation and treatment as a whole. Therefore, the device has various names due to the action, function and effect of curing various diseases, and due to the adopted structure, shape, theoretical deduction or some self-creation, however, it is still essentially an electrons emitting device.

DETAILED DESCRIPTION OF THE INVENTION

Figure 1:
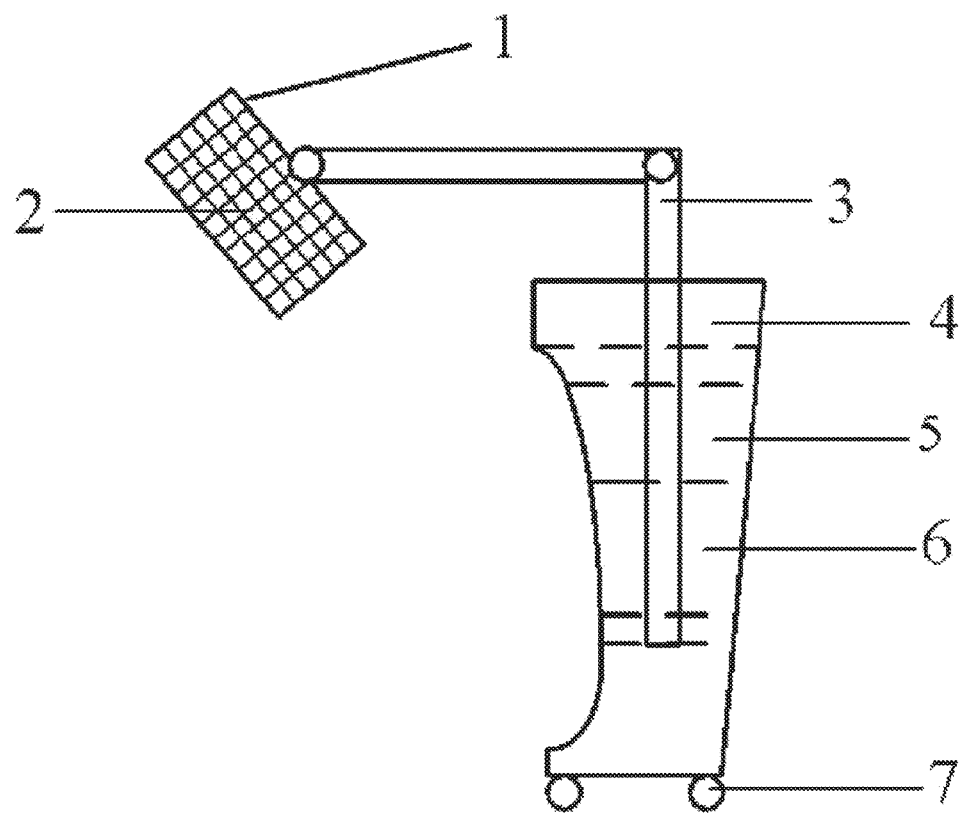
FIG. 1 is a structural schematic diagram of a medical electrons emitting device.

FIG. 1 is a structural schematic diagram of a medical electrons emitting device. An electrons emitting assembly 1 is connected with a support 3, the support 3 is connected with a housing and a box body 6, both a control system 4 and a power source are connected with the housing or the box body 6, the housing or the box body 6 is connected with a support wheel leg 7 or a support leg or a support plate 7; an electrons emitting electrode 2 is contained in the electrons emitting assembly 1.

Figure 2:
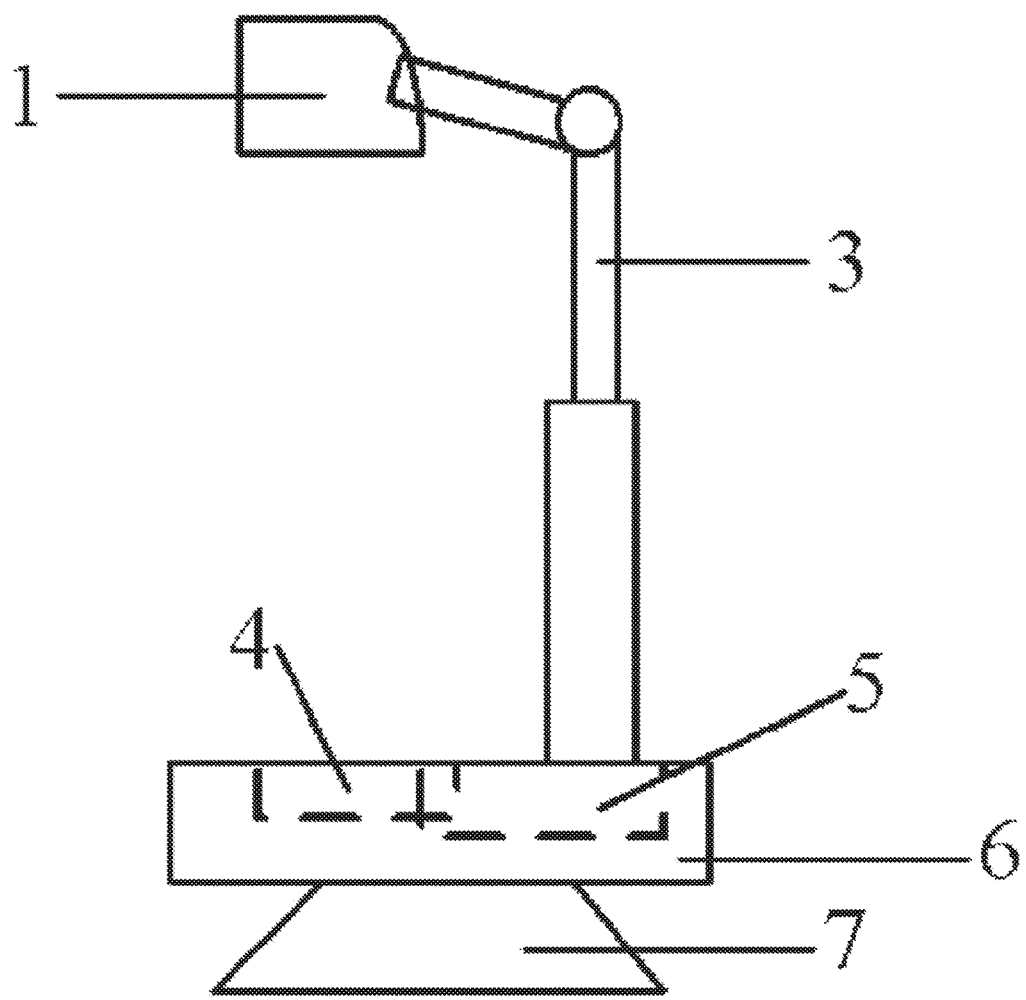
FIG. 2 is a structural schematic diagram of a household small-sized electrons emitting device.

FIG. 2 is a structural schematic diagram of a household small-sized electrons emitting device. The device can be folded and contracted, and similarly, is composed of an electrode emitting electrode 2, an electron emitting assembly 1, a retractable support 3, a control system 4, a power source 5, a housing or a box body 6, and a support leg 7.

Illustrative Examples of Clinical Application:

After years of clinical observation and the contrast of disease curing case, it is completely consistent, now the clinical cured cases are illustrated as follows:

1. Treatment of immune function deficiencies:

(1) Systemic lupus erythematosus: there is a 12-year-old boy who lives in Shijiazhuang City, Hebei Province and has won the first prize of National Hua Luogeng Mathematics Competition, has been diagnosed with systemic lupus erythematosus at a local hospital and a number of hospitals in Beijing, but his treatment is invalid. Hebei TV station calls on television ever to save this child. Before using the electrons emitting device, the patient has been taking hormones, but the symptoms become worse day by day, he feels a sharp pain in the part below double knee joint and cannot move on his own; and he is suffered from poor appetite, abdominal distension, indigestion, loose stools, screaming due to nightmares, twitched limbs and so on. When the patient uses the electrons emitting device for treatment at home, he was continuously treated (under natural breathing) by an emitting surface located at the outermost surface of the front part of the electrons emitting assembly 25 cm from a respiratory tract such as mouth and nose, and navel-abdomen (an area radially about 10 cm from the navel). From the date of treatment, the dosage of hormone is rapidly diminished according to the self-perception of the patient (progressively decreasing dosage by one half each time under normal circumstances with an observation period of one week, then going on decreasing progressively if there is no uncomfortable reaction). After treating for four days, the patient can get off from bed on his own. With the course of treatment, the symptoms are gradually reduced, and disappeared after three months. Through test, physiological indicators are returned to normal. The patient returns to normal life, and about six months later, he comes back to the classroom of the junior high school. After years of follow-up, the patient gets better. Later, the patient takes entrance examinations and was enrolled in a domestic famous university. As an additional note: the so-called continuous (natural breathing) treatment refers to using the electrons emitting device as much as possible except washing, eating, toileting, etc. The patient is in a natural breathing state and rest state when using the device. The patients of different conditions stay in hospital for different periods, usually between one month and three months. If the physiological parameters under test are returned to normal, the patient can carry a small therapeutic apparatus to return home and treat for a period of time to consolidate the curative effect. This description is equally applicable to the cases described below.

(2) Pemphigus: a 75-year-old man is diagnosed with pemphigus, (erythema, heat-humidity integration) but his treatment by the local provincial hospital is invalid, his condition becomes worse, which spreads to the eyes, nose, mouth, scrotum and body. His body is covered by bubbles densely, the pain is unbearable if the thin wall of a bubble is broken up, and it stenches. He is also suffered from diabetes mellitus, skin infections and purulent secretion. The application of traditional Chinese medicine and western medicine hormone fails to control the disease. He is terminally ill and notification of critical illness has been issued to his families. When being treated by the electrons emitting device, the patient is completely naked during the treatment. After continuous (natural breathing) treatment for 16 days, he is released from terminally ill. After a consolidation therapy for a few days, he is recovered and discharged. And a follow-up visit one year later shows that no recurrence happens.

(3) Baby diaper dermatitis: a seven-month old baby is suffered from diaper dermatitis from head to foot, and infected with sepsis. The drug therapy is invalid, so that the baby is in a critical condition. When being treated by the electrons emitting device, the baby is in bed and naked. The treatment is interrupted during daily care and feeding of the baby, so the treatment is carried out intermittently. And ten days later, the baby is recovered and discharged.

The above-mentioned cases are the diseases caused by immune function deficiencies, which cannot be cured by drugs currently. The above-mentioned critical diseases are treated using the electrons emitting device. The electrons entering the body activate the repairing genes in the dormant state due to the loss of electron to improve and repair the immune function of the body, so that the above-mentioned examples of critical diseases can be cured. Moreover, the method is simple and easy to realize when treating a patient without any adverse reaction, and the patient can be cured quickly and effectively.

2. Treatment of drug addiction abstinence syndrome: The clinical application to more than one hundred of heroin addicts in several anti-drug institutions shows that the use of the electrons emitting device for treatment makes the addicts feel happy and comfortable. The device can effectively reduce the drug addicts' nerve and physical dependence, and play a good role in drug treatment. As mentioned above, the use of the electrons emitting device for treatment can activate and recover the repairing gene of the body, so the effects on drug addiction abstinence syndrome are as following:

(1) The metabolism of the drug addicts is improved, so that the physiological function of the body may be recovered to be normal more quickly to promote rapid discharge of poisons from the body.

(2) Good sedative and hypnotic effects, wherein insomnia is the most common symptom of drug addicts during the course of detoxification and recovery, and its stubborn refractory often creates a vicious cycle in which drug addicts are unbearable and tends to relapse. Through the clinical observation, the drug addicts treated by the electrons emitting device enter into a deep sleep state within 10 m to 30 m.

(3) Conditioning a central nervous system and making it works better, promoting the release of endogenous opioid titanium; under normal physiological conditions, recovering the affinity between endogenous opioid substance secreted by the drug addicts and various opioid receptor, to a relatively constant foundation level; and gradually making the abstinence symptoms of drug addicts alleviated, resulting in abstinence.

(4) Conditioning the body of the drug addicts to balance a variety of physiological functions, so that the biological rhythm becomes normal, and at the same time the metabolic processes of the body is improved, and the drug addicts is recuperated quickly through replenishing the energy to the body.

The electrons emitting device for treatment of drug addiction abstinence is simple and convenient to use, and may significantly alleviate the suffering of drug addicts during the abstinence process, so that the abstinence process can be performed smoothly. During the recovery stage after detoxification, for example, a small domestic electrons emitting device therapy device can be used at home, the excitation and inhibition process of the central nervous system can be further adjusted; sleeping can be improved gradually, and anxiety and restlessness can be relieved; and the metabolism process can be adjusted and the physical fitness can be enhanced. In this way, the rate of relapse after drug abstinence will be reduced significantly, so as to increase the success rate of detoxification.

3. Treatment of diseases of respiratory system: through clinical observation, the electrons emitting device can improve the function of the respiratory system, and has a significant effect on a variety of bronchitis, acute and chronic pharyngitis, asthma, emphysema, silicosis and other diseases. In particular, it is the best cure for asthma, chronic obstructive pulmonary disease and other diseases that are difficult to cure.

Take asthma as an example, after the patient's condition is stable, the small domestic electrons emitting device is used at the rest time (such as sleep) at home every day, the patient only put it 20-30 cm away from where he's taking breath, under natural breathing, without other requirements. Hence it is convenient and simple to use, and after a period of conditioning, the patient can be cured.

4. Treatment of various traumas: it can be used for the clinical treatment of a variety of large area burns, scales, chemical injuries, swords and guns injuries as well as a variety of skin ulcers and infectious skin inflammation. The effects on these traumas have been confirmed in clinical treatment. During treatment, the wound of the patient is exposed about 20-30 cm away from the emitting surface at the outermost surface in the front of the electrons emitting assembly, under continuous (natural breathing) treatment for second deep degree or less of burns and scalds. Except for debridement and supplement of saline for the patients suffered from large area burns and scalds, it does not need to apply any medicine to the wounds, and it's faster to be recovered than applying the medicine. Its advantages are:

(1) Convenience and simpleness in use, and low cost.

(2) Superior performance in: disinfection for the local environment; wound sterilization; wound exudation control; promoting proliferation of epidermal stem cell; improving the body's metabolism and physiological environment; comprehensive treatment efficacy such as improving immune function.

(3) No infection occurs when it's properly used for trauma treatment, and the treatment process goes smoothly, treatment cycle is shortened, and the suffering of patients is greatly reduced.

(4) Particularly being conducive to rescue patients, especially the patients with trauma and a comprehensive chronic disease.

(5) In clinical treatment, more than once it cures the ulcers and wounds that cannot be cured by conventional drugs.

Through the above examples, we can conclude that the different cases of patients need to use different treatment methods and different electrons emitting devices with different electrons densities, and the density of emitting electrons directly changes the density of the negatively charged nano particles within the space range. According to different diseases, within the space range of 2.5 m$^3$ (2.5 meters long×1 meter wide×1 meter high) in the front of the electrons emitting assembly of the electrons emitting device, the density of the negatively charged nano particles has to reach up to more than $10^5$/cm$^3$, and less than or equal to $1.5\times10^9$/cm$^3$.

The examples above demonstrate that the curative effects on some diseases are superior to the existing drug therapies; and some of the diseases that cannot be cured by drugs can be cured. It is illustrated well that, with the use of the electrons emitting device for treatment, electrons can be effectively replenished to the body, the repairing genes of the body are activated and restored, the body's metabolic processes are improved to discharge harmful substances entering the body, the immunity of the body is enhanced, a two-way regulation is applied on the body and the external environment condition is improved, the natural physiological state and biochemical environment of the body are improved, and the internal environment condition is adjusted. Due to the natural environment where the human body stays and the by-products produced by metabolism, the DNA oxidative damage occurs at any time in the body, so that the prevention of these damages is one of the new and important measures to prevent cancers, genetic diseases and cell death. These effects are also applicable on both healthy and sub-healthy people, playing a role in preventing, conditioning and repairing. So this method is a new method of integrating prevention, care, treatment and recovery as a whole.

5. Treatment of cancer: for any cancer patient, the cancer cells beginning to spread in the body is the most panic turning point of condition. Modern medical research shows that less than 10% of deaths caused by cancer are not caused by the primary cancer and the other more than 90% of deaths are the result of the transfers of cancer cells to the important parts including lung, liver, bone and brain and so on.

Currently, chemotherapy and radiotherapy after operation, the latest measures such as tumor angiogenesis inhibitors, and drugs can appropriately extend the life of a patient with cancer metastasis, but was unable to reach a fundamental process of blocking cancer metastasis. The process of cancer metastasis is complicated. So far scientists in biomedical field are still trying to explore on this matter, but it is currently recognized by biosphere, that any cancer cells will enter the blood circulation through capillaries in the metastasis process. The electrons entering blood circulation reach all parts of the body, activate and repair the repairing genes of the body, including activating and repairing metastasis suppressor genes of various parts of the body. Most cancer cells transferred through capillary are killed by immune cells in the transfer process, and the metastasis suppressor genes will prevent escaping cancer cells from micrometastasis in constant rate and prevent the metastasis (spread) of cancer, while the immune cells will attack "foreign substances"—cancer cells that are not synthesized in vivo, to kill the cancer cells. Clinical practice shows that, operation is not necessary for early stage lung cancer patients, but they are directly treated by the electrons emitting device, and then the patients are cured and recovered. Due to the DNA oxidative damage, genetic mutation may be caused under certain conditions. The mutation is a main reason for cancers, genetic diseases and cell death, therefore, the cancer diseases should be treated from two aspects of prevention and treatment.

(1) Prevention: through observation among the crowds that are not seriously injured (such as suffered from nuclear radiation or invaded by heavy pollutants or suffered from seriously adverse bad life habits, etc.) and using the electrons emitting device at the rest time (during sleep, for example), no cancer patient is found. As already mentioned above, the use of electrons emitting device can improve the external environment condition, replenish the electrons as required for repairing the DNA oxidative damage of the body, regulate the internal and external environment condition in a two-way manner, and greatly reduce the incidence of cancers.

(2) Treatment: after treatment and removal of the primary cancer through a variety of therapies, drugs may be used to prevent the spread of cancer cells and the electrons emitting device may be used for treatment at the same time, the side effects of drugs may be significantly alleviated, and the spread of cancer cells may also be prevented at the same time. When the body is inspected that it returns to normal, the electrons emitting device may be stilled used for a long time at the rest time (such as during sleep) everyday, then it will continued to prevent the production and spread of cancer cells, and the body remains in a working condition of long-term health.

6. Treatment of AIDS: AIDS refers to acquired-immune-deficiency-syndrome, AIDS virus is also known as human immunodeficiency virus (HIV), up to now, as revealed by the research results of contemporary medicine, modern medicines, such as anti-retroviral drugs can suppress HIV, but it's unable to totally eliminate the proviruses hidden in the cells of patients. Some intact non-induced proviruses exist in cell nucleus of all parts of the body. Currently, the medical scientists believe that some of the proviruses may automatically resume activities, to duplicate their genetic substances and infect other cells. All of these intact non-induced proviruses need to be removed in order to cure AIDS, which requires special medication specifically for these proviruses, but there is no such drugs, and so far there is no way to completely cure AIDS through drugs. Statistics show that many patients with AIDS or HIV are accompanied by associated complications. As is already known through the previous examples, the following goals can be realized with the application of the electrons emitting device:

(1) In addition to the examples above, many diseases of immune function deficiency are cured, such as herpes virus, various ulcers, Candida albicans virus, bronchitis, septicemia and the like, which are included in the complications of the AIDS or the HIV carriers. The electrons emitting device will be the most powerful means of prevention and treatment of complications of HIV.

(2) The repairing genes of the body are repaired and activated, the vitality of the immune cells is improved, the "foreign substance"-virus that is not synthesized in vivo is attacked by the immune cells, and the provirus of the HIV hidden in the cell or tissue may be effectively killed.

Through the above examples as well as our long-term observation of clinical practice, the electrons emitting device may effectively improve the environment, and protect health; adjust and improve the internal environment condition of the body, and also repair and activate genes in the dormant state due to the loss of electrons, play a role in two-way regulation, in order to achieve a broad spectrum of medical function and effect. The therapeutic effects are far more than what are listed in the above examples. The device is continuously developed according to needs to play a greater role, and various dedicated devices can be made by different materials, structures, shapes and sizes. The device has various names due to the action, function and effect of curing various diseases, and due to the adopted structure, shape, theoretical deduction or some self-creation, however, it is still essentially an electrons emitting device.

In conclusion, if the three factors (correctly and effectively utilizing inhibiting functions of existing related drugs; accurately utilizing the functions of recuperation, regulation and energy replenishing of traditional Chinese medicine acupuncture point, traditional Chinese medicine and food therapy thereof; using the two-way regulation of the electrons emitting device, which improve an external environment condition and regulate and repair an internal environment condition) are well combined, the following goals can be realized: efficiently killing bacteria and viruses; regulating, improving and repairing complicated modes of a chemical radical in a histone, so as to accurately control the genes and coordinate information and activities of a whole genome; and repairing and activating a special repairing system of each tissue of the body; and a novel hopeful therapeutic scheme for treating AIDS or HIV carriers, cancers or cancer post-operation and various genetic diseases before histone codes are deciphered.

The invention claimed is:

1. A DNA oxidative damage repairing device, comprising a control system, a support, a power source, a housing and a box body, and a support wheel leg or a support plate, an electrons emitting electrode composed of a single electrode or a plurality of electrodes having a same potential, an electrons emitting assembly; wherein the electrons emitting electrode is contained in the electrons emitting assembly, the electrons emitting assembly is connected with the support, the support is connected with the housing or the box body, both the control system and the power source are connected with the housing or the box body, the housing or the box body is connected with the support wheel leg or the support plate;

wherein electrons are emitted by the electrons emitting electrode of the electrons emitting assembly of the device through a tunnel effect, the electrons emitting electrode is a unique electrode having a potential in the whole electrons emitting device with respect to a ground potential outside the device, the electrons emitting electrode is provided with a potential of −2 kv to −45 kv, the device only emits electrons to a space where the device is located, and does not emits any other substances, to form negatively charged nano particles with a density greater than $5 \times 10^3/cm^3$ and less than or equal to $1.5 \times 10^9/cm^3$ in an air space of greater than 20 m$^3$ and less than or equal to 100 m$^3$, such that bacteria and viruses in the air space are eliminated, and the air is sterilized; meanwhile, various contaminants and harmful substances suspended in the space are combined as particles of greater than 5 um, and the particles are sedimentated under gravity and electric field force so as to clean the environment of the air space; and the density of the negatively charged nano particle for a two-way regulation formed in a therapeutic area of 2.5 m$^3$ by 2.5 m long×1 m wide×1 m high in front of the electrons emitting assembly, is to be greater than $5 \times 10^3/cm^3$ and less than or equal to $1.5 \times 10^9/cm^3$, for replenishing the electrons lost due to DNA oxidative damage, and supplying electrons to the enzymes which offer the electrons for repairing oxidative damage in a repairing system at the same time.

* * * * *